United States Patent
Bourne et al.

(12) 
(10) Patent No.: US 11,602,586 B2
(45) Date of Patent: Mar. 14, 2023

(54) ASPIRATION SYSTEMS AND METHODS WITH MULTIPLE PUMPS AND PRESSURE SENSOR

(71) Applicant: Alcon Inc., Fribourg (CH)

(72) Inventors: John Morgan Bourne, Irvine, CA (US); Raphael Gordon, Ladera Ranch, CA (US); Gary P. Sorensen, Mission Viejo, CA (US)

(73) Assignee: Alcon Inc., Fribourg (CH)

( * ) Notice: Subject to any disclaimer, the term of this patent is extended or adjusted under 35 U.S.C. 154(b) by 44 days.

(21) Appl. No.: 17/063,007

(22) Filed: Oct. 5, 2020

(65) Prior Publication Data

US 2021/0100937 A1 Apr. 8, 2021

Related U.S. Application Data

(60) Provisional application No. 62/912,107, filed on Oct. 8, 2019.

(51) Int. Cl.
*A61M 1/00* (2006.01)
*A61F 9/007* (2006.01)

(52) U.S. Cl.
CPC ............... *A61M 1/74* (2021.05); *A61F 9/007* (2013.01); *A61M 2205/3331* (2013.01); *A61M 2210/0612* (2013.01)

(58) Field of Classification Search
CPC ............ A61M 1/74; A61M 2205/3331; A61M 2210/0612; A61M 2205/3351; A61M 2205/3355; A61M 1/0058; A61M 1/84; A61M 1/774; A61M 3/0258; A61M 1/77; A61M 2005/16863; A61M 2205/50; A61M 1/966; A61M 1/73; A61M 1/0023; A61M 1/14; A61M 1/3621; A61M 60/104; A61M 60/50; A61M 1/75; A61M 2205/123; A61M 2205/12; A61M 2205/128; A61M 3/0216; A61M 3/0283; A61M 1/00; A61M 3/022; A61M 1/1601; A61F 9/007;
(Continued)

(56) References Cited

U.S. PATENT DOCUMENTS 5,470,312 A 11/1995 Zanger et al.
5,676,650 A * 10/1997 Grieshaber ......... A61F 9/00736
417/205

(Continued)

*Primary Examiner* — Kai H Weng
*Assistant Examiner* — Brandon W. Levy
(74) *Attorney, Agent, or Firm* — Patterson + Sheridan, LLP

(57) ABSTRACT

Systems and methods for monitoring for an occlusion in an aspiration line during an ophthalmic surgical procedure. An ophthalmic surgical system may include a first aspiration pump located in a handpiece, a second aspiration pump located away from the handpiece such as in a console, and a pressure sensor located between the first aspiration pump and the second aspiration pump. The pressure sensor is adapted to monitor for an occlusion in the aspiration line upstream of the first aspiration pump. The second aspiration pump may be operated at the same flow rate as the first aspiration pump and/or to maintain a constant pressure between the second aspiration pump and the first aspiration pump. Systems and methods as disclosed allow for a handpiece pump located close to the working tip while providing reliable occlusion detection with a pressure sensor located away from the handpiece.

20 Claims, 2 Drawing Sheets

(58) Field of Classification Search
CPC .............. A61F 9/00745; A61F 9/00763; A61F 9/00736; A61B 2217/005; A61B 2217/007; A61B 2017/00973; A61B 3/16; A61B 2017/00411; A61B 2018/00636; F04B 43/12
See application file for complete search history.

(56) References Cited

U.S. PATENT DOCUMENTS

| | | | |
|---|---|---|---|
| 5,910,110 | A | 6/1999 | Bastable |
| 6,261,283 | B1 | 7/2001 | Morgan et al. |
| 6,293,926 | B1 | 9/2001 | Sorensen et al. |
| 6,572,349 | B2 | 6/2003 | Sorensen et al. |
| 6,632,214 | B2 | 10/2003 | Morgan |
| 6,740,074 | B2 | 5/2004 | Morgan |
| 6,902,542 | B2 | 6/2005 | Gordon |
| 6,962,488 | B2 | 11/2005 | Davis et al. |
| 7,393,189 | B2 | 7/2008 | Davis et al. |
| 7,775,780 | B2 | 8/2010 | Hopkins |
| 8,011,905 | B2 | 9/2011 | Artsyukhovich |
| 8,545,198 | B2 | 10/2013 | Artsyukhovich |
| 8,790,096 | B2 | 7/2014 | Sorensen |
| 9,482,216 | B2 | 11/2016 | Sorensen |
| 9,931,447 | B2 | 4/2018 | Layser |
| 2010/0191178 | A1 | 7/2010 | Ross et al. |
| 2010/0280434 | A1 | 11/2010 | Raney |
| 2012/0157912 | A1* | 6/2012 | Sorensen ............ A61F 9/00763 604/28 |
| 2014/0271251 | A1 | 9/2014 | Bourne et al. |
| 2015/0306286 | A1* | 10/2015 | Ross .................... A61M 1/743 604/22 |
| 2017/0367885 | A1* | 12/2017 | Bourne .................. A61M 1/74 |

* cited by examiner

ASPIRATION SYSTEMS AND METHODS WITH MULTIPLE PUMPS AND PRESSURE SENSOR

CROSS-REFERENCE TO RELATED APPLICATIONS

This application claims priority to and benefit of U.S. Provisional Patent Application No. 62/912,107, filed Oct. 8, 2019. The entire contents of each of these applications are incorporated by reference herein in their entirety.

TECHNICAL FIELD

The present disclosure is directed to aspiration systems and methods used, for example, during ophthalmic surgery.

BACKGROUND

In ophthalmic surgical procedures, fluids are often aspirated from the eye during the procedure. For example, in cataract surgery, a device may be used to fragment or emulsify a lens and to aspirate the broken or emulsified lens from the eye. As another example, in vitreoretinal surgery, a device may be used to aspirate vitreous material from the eye.

In addition, in some ophthalmic surgical procedures, it may be desirable to infuse fluid into the eye. For example, in cataract surgery, vitreoretinal surgery, or other procedures, a balanced salt solution or other irrigation fluid may be introduced into the eye. The irrigation fluid may be aspirated from the eye during the procedure.

Some known systems for performing ophthalmic surgical procedures include a handpiece that is held by the operator performing the procedure, wherein the handpiece is connected by one or more flexible conduits to a console. The operator holds the handpiece and introduces a working tip of the handpiece into the eye. In order to aspirate irrigation fluid and other material (e.g., broken or emulsified lens material or vitreous material) from the eye, the working tip of the handpiece has one or more openings connected through an aspiration channel to a flexible conduit that connects the handpiece to the console. The console houses a pump, such as a peristaltic pump, which produces a suction through the flexible conduit, whereby fluid and other material may be aspirated from the eye through the opening in the working tip of the handpiece, through the aspiration channel in the handpiece and flexible conduit, and into the console.

In some prior systems, the console includes a cassette that is loaded into a housing of the console. The cassette includes an elastomeric sheet joined to a rigid cassette body, wherein one or more fluid channels are formed in the space between the elastomeric sheet and the cassette body. For the pump, the console houses rollers mounted on a rotating hub. In operation, the pump rollers press the elastomeric sheet of the cassette to produce the pumping action.

In ophthalmic surgical procedures involving aspiration, it can be desirable to monitor the pressure of the fluid being aspirated as it is being aspirated. This can help the operator and/or the system to regulate the procedure, to monitor the intraocular pressure, and/or to determine if any partial or total occlusion is present in the aspiration line. In an example, a pressure sensor is located along the aspiration line in the console just upstream of the pump (i.e., in the console along the aspiration line in the direction of the handpiece). If an occlusion occurs, the pressure sensor detects a buildup of vacuum in the aspiration line.

References relating to fluid aspiration and/or pressure measurement in ophthalmic procedures include U.S. Pat. Nos. 6,261,283, 6,293,926, 6,572,349, 6,632,214, 6,740,074, 6,902,542, 6,962,488, 7,393,189, 7,775,780, 8,011,905, 8,545,198, 8,790,096, 9,482,216, and 9,931,447, the disclosures of which are hereby incorporated by reference herein in their entirety. Pressure sensors are additionally disclosed in U.S. Pat. Nos. 5,910,110 and 5,470,312, the disclosures of which are hereby incorporated by reference herein in their entirety.

Some designs have been proposed to locate the aspiration pump in the handpiece instead of the console. Locating the pump in the handpiece and therefore nearer to the working tip can minimize risks associated with occlusions and subsequent vacuum surges and can help achieve a steadier pressure which may improve chamber stability. U.S. Patent Application No. 2014/0271251 discloses various designs in which a pump is located in a handpiece. The disclosure of U.S. Patent Application No. 2014/0271251 is hereby incorporated by reference herein in its entirety.

When a pump is located in the handpiece close to the working tip, the distance between the pump and the working tip is relatively small. In addition, it is often desirable to make the handpiece as ergonomic as possible for ease of handling, thereby placing size, weight, and balance constraints on the handpiece. These factors can present challenges in monitoring the pressure between the handpiece pump and the working tip to determine if an occlusion occurs.

There is a continuing need for improved designs for aspiration systems and associated methods.

SUMMARY

The present disclosure is directed to improved aspirating systems of ophthalmic surgical systems and related methods.

In some example embodiments, an ophthalmic surgical system comprises a console; a handpiece comprising a working tip with an aspiration opening in the working tip, wherein the handpiece is connected to the console; an aspiration line comprising an aspiration channel in the handpiece, aspiration tubing between the handpiece and the console, and an aspiration channel in the console; a first aspiration pump located along the aspiration line in the handpiece; a second aspiration pump located along the aspiration line away from the handpiece; and a pressure sensor located along the aspiration line between the first aspiration pump and the second aspiration pump. The second aspiration pump may be located in the console. The pressure sensor may be located away from the handpiece, such as in the console. The use of a second aspiration pump and a pressure sensor between the first aspiration pump and the second aspiration pump enables the system to monitor for and detect occlusions upstream of the first aspiration pump in the handpiece, such as at the working tip.

In some example embodiments, an ophthalmic surgical system further comprises a controller. The controller may be configured to operate the second aspiration pump at the same flow rate as the first aspiration pump and/or to maintain a constant pressure between the second aspiration pump and the first aspiration pump. The controller may be configured to maintain a low vacuum level between the second aspiration pump and the first aspiration pump. The ophthalmic surgical system may further comprise an input control for an operator to input a selected vacuum level and/or a selected flow rate. The second aspiration pump and the first aspiration pump may be operated at the same flow rate based upon the vacuum level and/or flow rate from the input control.

In some example embodiments, a method of aspiration during an ophthalmic surgical procedure comprises operating a first aspiration pump located along an aspiration line in a handpiece; operating a second aspiration pump located along the aspiration line away from the handpiece; and monitoring a pressure in an aspiration line using a pressure sensor located along the aspiration line between the first aspiration pump and the second aspiration pump. The second aspiration pump may be operated at the same flow rate as the first aspiration pump. The second aspiration pump and the first aspiration pump may be operated to maintain a constant pressure between the second aspiration pump and the first aspiration pump. The second aspiration pump and the first aspiration pump may be operated to maintain a low vacuum level between the second aspiration pump and the first aspiration pump. The method may further comprises selecting a vacuum level and/or flow rate, wherein the second aspiration pump and the first aspiration pump are operated at the same flow rate based upon the selected vacuum level. The use of a second aspiration pump and a pressure sensor between the first aspiration pump and the second aspiration pump enables monitoring for and detecting occlusions upstream of the first aspiration pump in the handpiece, such as at the working tip.

As used herein with reference to an aspiration line, the terms "upstream" and "downstream" are used in reference to a direction of aspiration flow away from the eye. Thus, when a second component or object is located "upstream" of a first component or object, the second component is located along the aspiration line closer to the opening in the working tip than the first component. Thus, an occlusion located "upstream" of the aspiration pump in the handpiece is located along the aspiration line closer to the opening in the working tip than the aspiration pump in the handpiece (and, in fact, the occlusion may be located at the opening in the working tip).

The above examples and other examples will be understood by persons having ordinary skill in the art based on this disclosure.

BRIEF DESCRIPTION OF THE DRAWINGS

The accompanying drawings illustrate examples of the systems and methods disclosed herein and, together with the description, serve to explain the principles of the present disclosure.

The accompanying drawings may be better understood by reference to the following detailed description.

DETAILED DESCRIPTION

For the purposes of explaining the principles of the disclosure, reference is made to the drawings, and specific language is used to describe the same. It will nevertheless be understood that no limitation of the scope of the disclosure is intended. Any alterations and further modifications to the described systems, devices, instruments, and methods, and any further application of the principles of the present disclosure, are fully contemplated as would normally occur to one skilled in the art to which the disclosure relates. In particular, the features, components, and/or steps described with respect to one example of the disclosure may be combined with features, components, and/or steps described with respect to other examples of the disclosure. For simplicity, in some instances the same reference numbers are used throughout the drawings to refer to the same or like parts.

Figure 1:
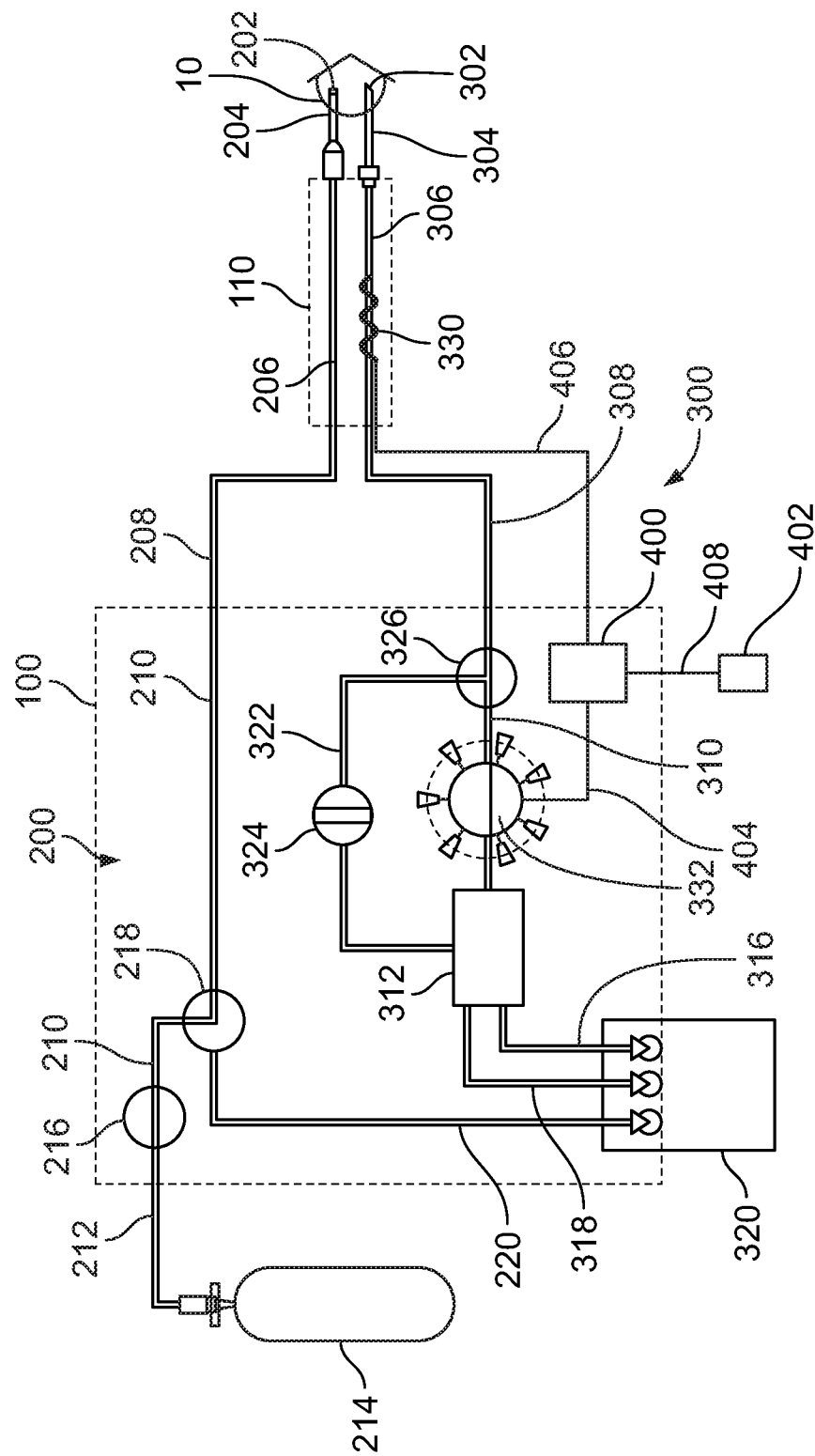
FIG. 1 is a schematic diagram illustrating components that may be utilized in systems and methods in accordance with the disclosure.

FIG. 1 is a schematic diagram illustrating some of the components that may be used in an ophthalmic surgical system, showing components of an irrigation system and an aspirating system. The example ophthalmic surgical system includes an ophthalmic surgical console 100. The ophthalmic surgical console 100 may comprise a housing and a fluidics cassette loaded into the housing. Except for differences as described herein, the ophthalmic surgical console may be similar to ophthalmic surgical consoles (including fluidics cassettes) as shown and described in U.S. Pat. No. 9,931,447, and/or to ophthalmic surgical consoles that have been known and used, such as the CENTURION® Vision System (including fluidics cassettes) available from Alcon Laboratories, Inc. (Fort Worth, Tex.) or the CONSTELLATION® Vision System (including fluidics cassettes) available from Alcon Laboratories, Inc. (Fort Worth, Tex.), or any other ophthalmic surgical consoles suitable for use with the principles described herein.

The console 100 includes one or more systems that may be used in performing an ophthalmic surgical procedure. For example, the console 100 includes components of a fluidics system that includes an irrigation system 200 for delivering fluid to the eye and an aspiration system 300 for aspirating fluid and/or other material from the eye. The console 100 also may include an ultrasonic generator system for driving an ultrasonic oscillation handpiece such as for phacoemulsification during cataract surgery and/or a pneumatic vitrectomy cutter system for driving a vitrectomy handpiece. The systems may overlap and cooperate to perform various aspects of the procedures.

In a typical setup, the ophthalmic surgical console 100 includes a housing having a computer system disposed therein and an associated display screen for showing data relating to system operation and performance during an ophthalmic surgical procedure. As mentioned above, the console may include a fluidics cassette, which may be loaded into the housing. In addition to the console 100, the ophthalmic surgical system may include one or more external devices for user operation, such as a foot pedal that an operator may use in controlling one or more functions. The foot pedal or other external operating device may communicate with the computer system of the console via a wired connection or wirelessly.

The example ophthalmic surgical system also includes a handpiece 110. The handpiece may be any suitable handpiece with an aspiration function, such as, for example, a phacoemulsification handpiece suitable for cataract surgery or a vitrectomy handpiece. The illustrated example handpiece 110 is a phacoemulsification handpiece with a working tip 304 for phacoemulsification and aspiration. In other examples, the working tip 304 may be a needle such as a vitrectomy needle. The working tip 304 has an opening 302 in its distal end for aspirating fluid and other material from the eye 10. The handpiece 110 also has an irrigation tube 204 with an opening 202 in its distal end for delivering irrigation fluid to the eye 10. The irrigation tube 204 may be a flexible sleeve that is disposed around the working tip 304 of the handpiece 110.

The handpiece 110 is connected to the console 100 by one or more flexible conduits that comprise or house irrigation tubing 208 for delivering irrigation fluid from the console 100 to the handpiece 110, aspiration tubing 308 for delivering aspirated fluid and other materials from the handpiece 110 to the console 100, and/or electrical wiring 406 for electrical communication between the console 100 and the handpiece 110.

The example ophthalmic surgical system further includes an irrigation source 214 which may be included in the console 100 or may be a separate component connected to the console 100 by tubing 212. The irrigation source 214 may be a sterile solution reservoir, such as for holding a balanced salt solution for delivering to the eye 10. Other fluids may be used.

The example irrigation system 200 extends between the irrigation source 214 and the handpiece 110 and carries irrigating fluid through the irrigation flow path to the surgical site (eye 10) during the surgical procedure. The irrigation source 214 may be a mechanically pressurized fluid source such as, for example, an irrigation bag compressed by a clamping pressure system. In other embodiments, the irrigation source 214 may be a source suspended by a pole (e.g., an irrigation bag suspended by an IV pole), which may or may not be adjustable. Other fluid sources may be used as the irrigation source 214.

The irrigation system 200 may further comprise an irrigation valve 218 that regulates flow from the irrigation source 214 to the surgical site, an irrigation channel 210 in the console 100 (in the housing and/or cassette), irrigation tubing 208 between the console 100 and the handpiece 110, an irrigation channel 206 in the handpiece 110, and the irrigation tube or sleeve 204 (which may be considered a component of the handpiece 110).

In some embodiments, the irrigation tubing 208 is formed of multiple segments, with some segments being rigid and others being flexible. Also, in some embodiments, at least a portion of the irrigation system 200 is formed in a cassette that is loaded into the console housing to provide fluid communication between the irrigation source 214 and the patient's eye 10. The pressure of the fluid in the irrigation flow path may be monitored via a pressure sensor 216 in the console (in the housing and/or cassette).

The irrigation valve 218 may selectively allow or block flow from the irrigation source 214 to the handpiece 110 and into the eye 10. In some examples, the irrigation valve 218 also may allow flow to a shunt path 220 and into a drain 320. In some examples, the irrigation valve 218 is adjustable to control the rate of flow from the irrigation source 214 to the handpiece 110 and into the eye 10.

The example aspiration system 300 includes an opening 302 in the working tip 304, an aspiration channel 306 through the handpiece 110 (including through the working tip 304), aspiration tubing 308 between the handpiece 110 and the console 100, an aspiration channel 310 in the console 100 (in the housing and/or cassette), a vent line 322 with a vent valve 324, a vent reservoir 312, a drain 320 such as a drain bag, and tubing 316, 318 to the drain 320. The drain 320 may be a bag or any suitable container, and, in some embodiments, it may be a drain to piping or tubing instead of a self-contained reservoir.

As can be seen, the aspiration system 300 comprises an aspiration fluid path that extends from the surgical site (eye 10) to the drain 320. The aspiration system 300 is used to aspirate fluid as well as any other materials to be aspirated from the eye, such as emulsified particles or vitreous fibers, through the aspiration flow path out of the eye 10 during the surgical procedure.

In some embodiments, the aspiration tubing 308 is formed of multiple segments, with some segments being rigid and others being flexible. Also, in some embodiments, at least a portion of the aspiration system 300 is formed in a cassette that is part of the console 100.

As can be seen in FIG. 1, the aspiration system 300 includes a handpiece pump 330. The handpiece pump 330 may be, for example, a peristaltic pump that acts on a flexible portion of the aspiration channel 306 within the handpiece 110. The pumping action of the handpiece pump 330 may be provided, for example, by one or more helical ridges mounted on a rotor or by one or more rollers. The handpiece pump 330 provides sufficient vacuum pressure to aspirate any fluid or tissue that is desired to be aspirated from the eye (e.g., emulsified lens tissue, vitreous fibers).

The action of the handpiece pump 330 is controlled by a controller 400 that communicates with handpiece pump 330 by electrical wiring 406 that connects the handpiece pump 330 to the controller 400. Alternatively, the controller 400 may be in wireless communication with the handpiece pump 330. An input control 402 allows the operator to select a desired vacuum pressure and/or a desired flow rate for aspiration. The input control 402 may include any suitable input mechanism, such as a dial, pushbutton(s), touchscreen, and the like. The input control 402 may be in communication with the controller 400 by electrical wiring 408 that connects the input control 402 to the controller 400. Alternatively, the controller 400 may be in wireless communication with the input control 402. Based on the input from the input control 402, the controller 400 controls the action of the handpiece pump 330.

In order to monitor pressure in the aspiration line, including pressure upstream of the handpiece pump 330 (i.e., between the handpiece pump 330 and opening 302 in the working tip 304), the aspiration system 300 of FIG. 1 includes a second pump 332 located in the console 100 and in series along the aspiration line with the handpiece pump 330, with a pressure sensor 326 located along the aspiration line between the two pumps 332, 330. The second pump 332 may be, for example, a peristaltic pump that acts on a flexible portion of the aspiration channel 310 within the console 100 (in the housing and/or cassette). The pumping action of the second pump 332 may be provided, for example, by one or more rollers mounted on a rotating hub or by one or more helical ridges mounted on a rotor. For example, a set of rollers may be radially mounted from an axis of rotation of a peristaltic pump motor (e.g., a stepper or direct current (DC) servo motor, or other motor (such as an alternating current (AC) motor)) and may be configured to compress a flexible portion of the aspiration channel 310 (such as the pump segments of an elastomeric sheet mounted on a cassette body). The action of the second pump 332, e.g., the action of the motor of the second pump 332, is controlled by the controller 400. The controller 400 communicates with the second pump 332 by electrical wiring 404 that connects the second pump 332 to the controller 400. Alternatively, the controller 400 may be in wireless communication with the second pump 332.

The pressure sensor 326 is located along the aspiration flow path between the second pump 332 and the handpiece pump 330. Considering the direction of aspiration flow from the eye 10 to the drain 320, the pressure sensor is located upstream of the second pump 332 and downstream of the handpiece pump 330. In the illustrated embodiment of FIG. 1, the pressure sensor 326 is located in the console 100 (housing and/or cassette). Alternatively, the pressure sensor may be located outside of the console 100 at another location along the aspiration flow path between the second pump 332 and the handpiece pump 330.

The pressure sensor 326 may be any suitable sensor capable of sensing the pressure in the aspiration flow path between the two pumps 332, 330. Example pressure sensors include pressure sensors using a load cell to measure deflection of a diaphragm in contact with the fluid and pressure sensors using optical measurement of deflection of a diaphragm in contact with the fluid, among others.

The controller 400 may include a processor and memory that may include an executable program for preforming various functions such as detecting information received from the input control 402, operating the handpiece pump 330, operating the second pump 332, detecting information received from the pressure sensor 326, and operating the vent valve 324.

In one example, the controller 400 is a PID controller configured to control the handpiece pump 330, the second pump 332, and/or the vent valve 324 to mitigate pressure deviations, such as upon the occurrence of an occlusion or upon the occurrence of a surge after clearance of an occlusion. The controller 400 may include one or more pre-established pressure thresholds establishing desired pressure limits. The pre-established pressure thresholds may be different for different pressure selections made by the operator through the input control 402. These thresholds may be input by an operator or may be preset and stored during manufacturing. When the measured or detected pressure from the pressure sensor 326 passes beyond these pre-established thresholds, the controller 400 controls the handpiece pump 330, the second pump 332, and/or the vent valve 324 to restore the pressure to a desired level.

In accordance with the disclosure herein, the second pump 332 is operated to produce the same flow rate through the aspiration line as the handpiece pump 330. That is, the handpiece pump 330 is pumping fluid toward the second pump 332 at the same rate as the second pump 332 is pumping fluid. In this way, the vacuum pressure level between the two pumps is held constant or relatively constant. When the operator selects a desired pressure level and/or flow rate through the input control 402, the controller 400 then operates the handpiece pump 330 to achieve that selected pressure level and/or flow rate, and the controller operates the second pump 332 to have the same flow rate as the handpiece pump 330.

When the aspiration pathway is occluded, such as when lens fragments enter and clog portions of the aspiration pathway during a surgery, the surgical system may detect the vacuum, or pressure difference, via the pressure sensor 326. A common location for an occlusion to happen is at or near the opening 302 of the working tip 304. Such an occlusion will cause a vacuum buildup in the area between the handpiece pump 330 and the opening 302 of the working tip 304. As a result, due to the continued operation of the second pump 332, a vacuum buildup will also occur between the handpiece pump 330 and the second pump 332, which will be detected by the pressure sensor 326.

Accordingly, with a system as disclosed herein, including in the example illustrated in FIG. 1, the system can monitor for an occlusion in the working tip 304 or anywhere upstream of the handpiece pump 330 by the pressure sensor 326 located downstream from the handpiece pump 330, between the handpiece pump 330 and the second pump 332. That is, when an occlusion event occurs upstream of the handpiece pump 330, the reduced flow in the aspiration line between the two pumps 330, 332 will result in a drop in pressure. This is detected by the pressure sensor 326, providing an indirect measurement of the pressure upstream of the handpiece pump 330. With a system as disclosed herein, including in the example illustrated in FIG. 1, the system can monitor for and detect an occlusion without the need for a pressure sensor located upstream of the handpiece pump 330, between the handpiece pump 330 and the opening 302 of the working tip 304.

Figure 2:
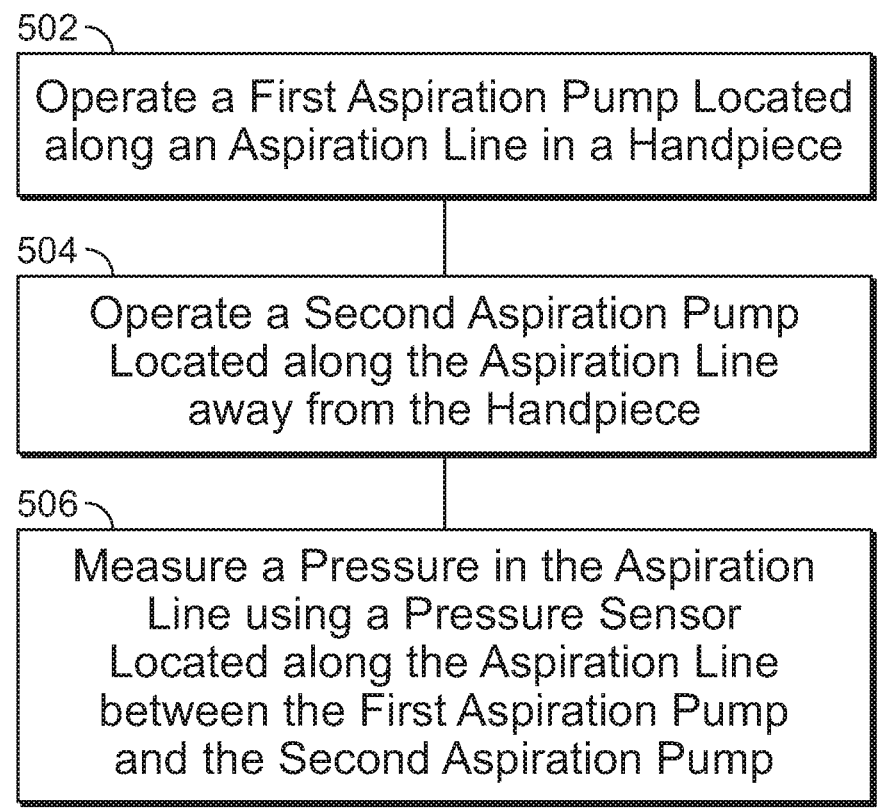
FIG. 2 is a flow chart showing steps in an example method in accordance with the disclosure.

FIG. 2 is a flow chart showing steps in an example method in accordance with the disclosure. In a first step 502, a first aspiration pump located along an aspiration line in a handpiece is operated to aspirate fluid and/or other materials (e.g., tissue such as emulsified lens material) from the eye. The first aspiration pump may be a handpiece pump such as the handpiece pump 330 shown in FIG. 1. In a second step 504, which may be performed simultaneously with the first step 502, a second aspiration pump located along the aspiration line away from the handpiece is operated to further pump the fluid and/or other materials that were pumped by the first aspiration pump. The second aspiration pump may be a pump such as the second pump 330 shown in FIG. 1. The second aspiration pump is positioned along the aspiration line in series with the first aspiration pump; the second aspiration pump is positioned downstream from the first aspiration pump. In a third step 506, which is performed while the first aspiration pump and the second aspiration pump are operating, a pressure in the aspiration line is measured using a pressure sensor located along the aspiration line between the first aspiration pump and the second aspiration pump. The pressure sensor may be a pressure sensor such as the pressure sensor 326 in FIG. 1. The use of a second aspiration pump and a pressure sensor between the first aspiration pump and the second aspiration pump enables monitoring for and detecting occlusions upstream of the first aspiration pump in the handpiece, such as at the working tip.

The second aspiration pump may be operated at the same flow rate as the first aspiration pump. The second aspiration pump and the first aspiration pump may be operated to maintain a constant pressure between the second aspiration pump and the first aspiration pump. The second aspiration pump and the first aspiration pump may be operated to maintain a low vacuum level between the second aspiration pump and the first aspiration pump. In alternative embodiments, the second aspiration pump and the first aspiration pump may be operated to maintain pressure at an atmospheric pressure level between the second aspiration pump and the first aspiration pump. The method may further comprise selecting a vacuum level and/or flow rate, wherein the second aspiration pump and the first aspiration pump are operated at the same flow rate based upon the selected vacuum level and/or flow rate. For example, an operator may select a vacuum level and/or flow rate using an input control such as input control 402, and the second aspiration pump and the first aspiration pump may be operated at the same flow rate based upon the selected vacuum level.

Systems and methods as disclosed herein have one or more advantages as compared to prior systems and methods. For example, embodiments of systems and methods as disclosed herein allow monitoring for and detecting occlusions upstream of a handpiece pump (such as at the working tip) without the need for a pressure sensor in the handpiece, resulting in simpler designs and lower costs. Embodiments of systems and methods as disclosed herein also can allow improved ergonomics of the handpiece as compared to designs requiring a pressure sensor in the handpiece. Embodiments of systems and methods as disclosed herein can avoid handpiece size, weight, and balance issues that can arise in designs requiring a pressure sensor in the handpiece.

Persons of ordinary skill in the art will appreciate that the implementations encompassed by the disclosure are not limited to the particular exemplary implementations described above. In that regard, although illustrative implementations have been shown and described, a wide range of modification, change, and substitution is contemplated in the foregoing disclosure. It is understood that such variations may be made to the foregoing without departing from the scope of the disclosure. Accordingly, it is appropriate that the appended claims be construed broadly and in a manner consistent with the disclosure.

What is claimed is:

1. An ophthalmic surgical system comprising:
a console;
a handpiece comprising a working tip with an aspiration opening in the working tip, wherein the handpiece is connected to the console;
an aspiration line comprising an aspiration channel in the handpiece, aspiration tubing between the handpiece and the console, and an aspiration channel in the console;
a first aspiration pump located along the aspiration line in the handpiece;
a second aspiration pump located along the aspiration line away from the handpiece;
a pressure sensor located along the aspiration line between the first aspiration pump and the second aspiration pump, wherein the pressure sensor is adapted to monitor for an occlusion in the aspiration line upstream of the first aspiration pump; and
a controller configured to control the operation of the first aspiration pump and the second aspiration pump based on a pressure reading from the pressure sensor, the pressure reading indicating a difference in pressure within the aspiration line between the first aspiration pump and the second aspiration pump.

2. An ophthalmic surgical system as in claim 1, wherein the second aspiration pump is located in the console.

3. An ophthalmic surgical system as in claim 1, wherein the pressure sensor is located away from the handpiece.

4. An ophthalmic surgical system as in claim 1, wherein the pressure sensor is located in the console.

5. An ophthalmic surgical system as in claim 1, wherein the controller is configured to operate the second aspiration pump at a same flow rate as the first aspiration pump.

6. An ophthalmic surgical system as in claim 1, wherein the controller is configured to operate the second aspiration pump and the first aspiration pump to maintain a constant pressure between the second aspiration pump and the first aspiration pump.

7. An ophthalmic surgical system as in claim 1, wherein the controller is configured to operate the second aspiration pump and the first aspiration pump to maintain a preset vacuum level between the second aspiration pump and the first aspiration pump.

8. An ophthalmic surgical system as in claim 1, wherein the ophthalmic surgical system further comprises an input control for an operator to input a selected vacuum level or flow rate, and wherein the second aspiration pump and the first aspiration pump are operated at the same flow rate based upon the vacuum level or flow rate from the input control.

9. An ophthalmic surgical system comprising:
a console;
a handpiece comprising a working tip with an aspiration opening in the working tip, wherein the handpiece is connected to the console;
an aspiration line comprising an aspiration channel in the handpiece, aspiration tubing between the handpiece and the console, and an aspiration channel in the console;
a first aspiration pump located along the aspiration line in the handpiece;
a second aspiration pump located along the aspiration line away from the handpiece;
a pressure sensor located along the aspiration line between the first aspiration pump and the second aspiration pump;
an input control for an operator to input a selected vacuum level or flow rate; and
a controller, wherein the controller is configured to operate the second aspiration pump and the first aspiration pump at the same flow rate based upon the vacuum level or flow rate from the input control, the controller further configured to operate the first aspiration pump and the second aspiration pump based on a pressure reading from the pressure sensor, the pressure reading indicating a difference in pressure within the aspiration line between the first aspiration pump and the second aspiration pump;
wherein the pressure sensor is adapted to monitor for an occlusion in the aspiration line upstream of the first aspiration pump.

10. An ophthalmic surgical system as in claim 9, wherein the second aspiration pump is located in the console.

11. An ophthalmic surgical system as in claim 9, wherein the pressure sensor is located away from the handpiece.

12. An ophthalmic surgical system as in claim 9, wherein the pressure sensor is located in the console.

13. A method of monitoring for an occlusion in an aspiration line during an ophthalmic surgical procedure, the method comprising:
operating a first aspiration pump located along an aspiration line in a handpiece;
operating a second aspiration pump located along the aspiration line away from the handpiece;
monitoring a pressure in the aspiration line using a pressure sensor located along the aspiration line between the first aspiration pump and the second aspiration pump, thereby monitoring for an occlusion in the aspiration line upstream of the first aspiration pump and
controlling the operation of the first aspiration pump and the second aspiration pump based on the monitored pressure, the monitored pressure indicating a difference in pressure within the aspiration line between the first aspiration pump and the second aspiration pump.

14. A method of monitoring for an occlusion in an aspiration line during an ophthalmic surgical procedure as in claim 13, wherein the second aspiration pump is located in a console.

15. A method of monitoring for an occlusion in an aspiration line during an ophthalmic surgical procedure as in claim 13, wherein the pressure sensor is located away from the handpiece.

16. A method of monitoring for an occlusion in an aspiration line during an ophthalmic surgical procedure as in claim 13, wherein the pressure sensor is located in a console.

17. A method of monitoring for an occlusion in an aspiration line during an ophthalmic surgical procedure as in claim 13, wherein the second aspiration pump is operated at a same flow rate as the first aspiration pump.

18. A method of monitoring for an occlusion in an aspiration line during an ophthalmic surgical procedure as in claim 13, wherein the second aspiration pump and the first aspiration pump are operated to maintain a constant pressure between the second aspiration pump and the first aspiration pump.

19. A method of monitoring for an occlusion in an aspiration line during an ophthalmic surgical procedure as in claim 13, wherein the second aspiration pump and the first aspiration pump are operated to maintain a preset vacuum level between the second aspiration pump and the first aspiration pump.

20. A method of monitoring for an occlusion in an aspiration line during an ophthalmic surgical procedure as in claim 13, further comprising selecting a vacuum level or flow rate, wherein the second aspiration pump and the first aspiration pump are operated at the same flow rate based upon the selected vacuum level or flow rate.

* * * * *